(12) United States Patent
McDonald et al.

(10) Patent No.: US 8,674,178 B2
(45) Date of Patent: Mar. 18, 2014

(54) PRODUCTION OF CELLULASE ENZYMES IN PLANT HOSTS USING TRANSIENT AGROINFILTRATION

(75) Inventors: Karen A. McDonald, Davis, CA (US); Benjamin E. Lindenmuth, Davis, CA (US); Abhaya M. Dandekar, Davis, CA (US); Bryce W. Falk, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 228 days.

(21) Appl. No.: 12/544,195

(22) Filed: Aug. 19, 2009

(65) Prior Publication Data

US 2010/0055740 A1 Mar. 4, 2010

Related U.S. Application Data

(60) Provisional application No. 61/090,221, filed on Aug. 19, 2008.

(51) Int. Cl.
| | |
|---|---|
| *A01H 5/00* | (2006.01) |
| *A01H 5/10* | (2006.01) |
| *C12N 15/82* | (2006.01) |
| *C12N 15/84* | (2006.01) |
| *C12P 21/04* | (2006.01) |
| *C12N 15/56* | (2006.01) |
| *C12N 15/62* | (2006.01) |
| *C12N 15/31* | (2006.01) |

(52) U.S. Cl.
USPC ........ 800/288; 800/294; 800/317.3; 800/287; 435/69.8; 435/70.1; 435/469; 435/414; 435/209

(58) Field of Classification Search
None
See application file for complete search history.

(56) References Cited

U.S. PATENT DOCUMENTS

| 5,275,944 A | 1/1994 | Himmel et al. |
| 6,818,803 B1 * | 11/2004 | Austin-Phillips et al. .... 800/278 |
| 2001/0047526 A1 * | 11/2001 | Brisson et al. ................ 800/298 |
| 2003/0135885 A1 | 7/2003 | Lanahan et al. |
| 2007/0250961 A1 | 10/2007 | Blaylock et al. |
| 2008/0078005 A1 | 3/2008 | Lebel et al. |
| 2009/0068644 A1 * | 3/2009 | Bendahmane et al. .......... 435/6 |

FOREIGN PATENT DOCUMENTS

WO WO/2006/010646 * 2/2006

OTHER PUBLICATIONS

Dashek, Methods in Plant Biochemistry and Molecular Biology, CRC Press 1997.*
Dai et al (Transgenic Research (9)43-54, 2000).*
Sun et al (Bioresource Technology 98 (2007) 2866-2872.*
Acta Biochemica Polonica, vol. 53 No. 2/2006, 289-98—see p. 289, right column, second paragraph, lines 1-7.*
Kalantidis at al. (Dec. 2007). "Virp1 is a Host Protein with a Major Role in *Potato Spindle Tuber Viroid* Infection in *Nicotiana* Plants," Journal of Virology 81(23):12872-12880.
International Search Report and Written Opinion mailed on Oct. 30, 2009, for PCT Patent Application No. PCT/US2009/54359, filed Aug. 19, 2009. 7 pages.
International Preliminary Report on Patentability received for PCT Patent Application No. PCT/US2009/054359, mailed on Mar. 3, 2011, 6 pages.

* cited by examiner

*Primary Examiner* — David T Fox
*Assistant Examiner* — Lee A Visone
(74) *Attorney, Agent, or Firm* — Morrison & Foerster LLP

(57) ABSTRACT

Described herein are methods useful for producing proteins, such as enzymes, by agrofiltration. The methods involve producing an *Agrobacterium* with a Ti plasmid encoding a cellulase, infecting plant cells with the *Agrobacterium*, allowing expression of the cellulase, and recovering the cellulase from the plant cells. In one embodiment, the protein produced is an endoglucanase.

21 Claims, 13 Drawing Sheets

MKNTSSLCLLLVLCSLTCNSGQA AGGGYWHTSGREILD
ANNVPVRIAGINVFGFETCNYVVHGLWSRDYRSMLDQIKSL
GYNTIRLPYSDDILKPGTMPNSINFYQMNQDLQGLTSLQVM
DKIVAYAGQIGLRIILDRHRPDCSGQSALWYTSSVSEATWIS
DLQALAQRYKGNPTVVGFDLHNEPHDPACWGCGDPSIDV
RLAAERAGNVLSVNPNLLIFVEGVQSYNGDSYWWGGNLQG
AGQYPVVLNVPNRLVYSAHDYATSVYPQTWFSDPTFPNNM
PGIWNKNWGYLFNQNIAPVWLGEFGTTLQSTTDQTWLKTL
VQYLRPTAQYGADSFQWTFWSWNPDSGDTGGILKDDWQT
VDTVKDGYLAPIKSSIFDPVGASASPSSQPSPSVSPSPSPSP
SASRTPTPTPTPTASPTPTLTPTATPTPTASPTPSPTAASGA
RCTAS YQVNSDWGNGFTVTVAVTNSGSVATKTWTVSWTF
GGNQTITNSWNAAVTQNGQSVTARNMSYNNVIQPGQNTTF
GFQASYTGSNAAPTVACAAS His-Tag

Ramy3D signal Peptide (at start)

E1 – β1,4-endoglucanase from *Acidothermus cellulolyticus*

Figure 2

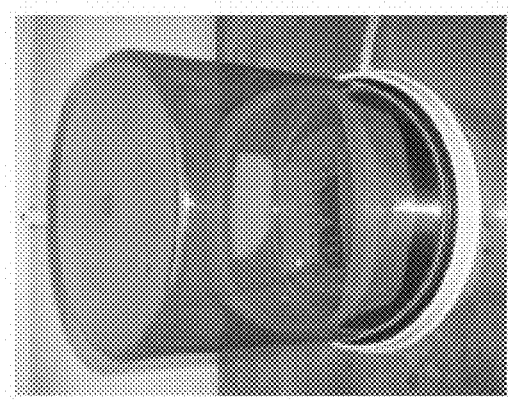
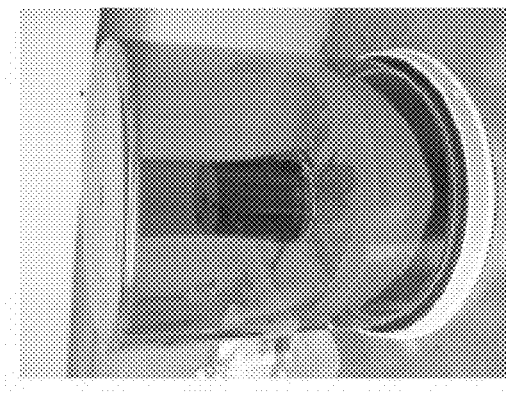
Figure 12

SEQUENCE LISTING

<160> NUMBER OF SEQ ID NOS: 3

<210> SEQ ID NO 1
<211> LENGTH: 25
<212> TYPE: PRT
<213> ORGANISM: Acidothermus cellulolyticus

<400> SEQUENCE: 1

Met Lys Asn Thr Ser Ser Leu Cys Leu Leu Leu Val Val Leu Cys
1               5                   10                  15

Ser Leu Thr Cys Asn Ser Gly Gln Ala
            20                  25

<210> SEQ ID NO 2
<211> LENGTH: 520
<212> TYPE: PRT
<213> ORGANISM: Acidothermus cellulolyticus

<400> SEQUENCE: 2

Ala Gly Gly Gly Tyr Trp His Thr Ser Gly Arg Glu Ile Leu Asp Ala
1               5                   10                  15

Asn Asn Val Pro Val Arg Ile Ala Gly Ile Asn Trp Phe Gly Phe Glu
            20                  25                  30

Thr Cys Asn Tyr Val Val His Gly Leu Trp Ser Arg Asp Tyr Arg Ser
            35                  40                  45

Met Leu Asp Gln Ile Lys Ser Leu Gly Tyr Asn Thr Ile Arg Leu Pro
        50                  55                  60

Tyr Ser Asp Asp Ile Leu Lys Pro Gly Thr Met Pro Asn Ser Ile Asn
65                  70                  75                  80

Phe Tyr Gln Met Asn Gln Asp Leu Gln Gly Leu Thr Ser Leu Gln Val
            85                  90                  95

Met Asp Lys Ile Val Ala Tyr Ala Gly Gln Ile Gly Leu Arg Ile Ile
            100                 105                 110

Leu Asp Arg His Arg Pro Asp Cys Ser Gly Gln Ser Ala Leu Trp Tyr
        115                 120                 125

Thr Ser Ser Val Ser Glu Ala Thr Trp Ile Ser Asp Leu Gln Ala Leu
130                 135                 140

Ala Gln Arg Tyr Lys Gly Asn Pro Thr Val Val Gly Phe Asp Leu His
145                 150                 155                 160

Asn Glu Pro His Asp Pro Ala Cys Trp Gly Cys Gly Asp Pro Ser Ile
            165                 170                 175

Asp Trp Arg Leu Ala Ala Glu Arg Ala Gly Asn Val Leu Ser Val Asn
        180                 185                 190

Pro Asn Leu Leu Ile Phe Val Glu Gly Val Gln Ser Tyr Asn Gly Asp
            195                 200                 205

Ser Tyr Trp Trp Gly Gly Asn Leu Gln Gly Ala Gly Gln Tyr Pro Val
        210                 215                 220

Val Leu Asn Val Pro Asn Arg Leu Val Tyr Ser Ala His Asp Tyr Ala
225                 230                 235                 240

Thr Ser Val Tyr Pro Gln Thr Trp Phe Ser Asp Pro Thr Phe Pro Asn
            245                 250                 255

Asn Met Pro Gly Ile Trp Asn Lys Asn Trp Gly Tyr Leu Phe Asn Gln
        260                 265                 270

Asn Ile Ala Pro Val Trp Leu Gly Glu Phe Gly Thr Thr Leu Gln Ser
        275                 280                 285

-continued

```
Thr Thr Asp Gln Thr Trp Leu Lys Thr Leu Val Gln Tyr Leu Arg Pro
    290                 295                 300

Thr Ala Gln Tyr Gly Ala Asp Ser Phe Gln Trp Thr Phe Trp Ser Trp
305                 310                 315                 320

Asn Pro Asp Ser Gly Asp Thr Gly Gly Ile Leu Lys Asp Asp Trp Gln
                325                 330                 335

Thr Val Asp Thr Val Lys Asp Gly Tyr Leu Ala Pro Ile Lys Ser Ser
            340                 345                 350

Ile Phe Asp Pro Val Gly Ala Ser Ala Ser Pro Ser Ser Gln Pro Ser
        355                 360                 365

Pro Ser Val Ser Pro Ser Pro Ser Pro Ser Pro Ser Ala Ser Arg Thr
    370                 375                 380

Pro Thr Pro Thr Pro Thr Pro Thr Ala Ser Pro Thr Pro Thr Leu Thr
385                 390                 395                 400

Pro Thr Ala Thr Pro Thr Pro Thr Ala Ser Pro Thr Pro Ser Pro Thr
                405                 410                 415

Ala Ala Ser Gly Ala Arg Cys Thr Ala Ser Tyr Gln Val Asn Ser Asp
            420                 425                 430

Trp Gly Asn Gly Phe Thr Val Thr Val Ala Val Thr Asn Ser Gly Ser
        435                 440                 445

Val Ala Thr Lys Thr Trp Thr Val Ser Trp Thr Phe Gly Gly Asn Gln
    450                 455                 460

Thr Ile Thr Asn Ser Trp Asn Ala Ala Val Thr Gln Asn Gly Gln Ser
465                 470                 475                 480

Val Thr Ala Arg Asn Met Ser Tyr Asn Asn Val Ile Gln Pro Gly Gln
                485                 490                 495

Asn Thr Phe Phe Gly Phe Gln Ala Ser Tyr Thr Gly Ser Asn Ala Ala
            500                 505                 510

Pro Thr Val Ala Cys Ala Ala Ser
        515                 520

<210> SEQ ID NO 3
<211> LENGTH: 6
<212> TYPE: PRT
<213> ORGANISM: Acidothermus cellulolyticus

<400> SEQUENCE: 3

His His His His His His
1               5
```

PRODUCTION OF CELLULASE ENZYMES IN PLANT HOSTS USING TRANSIENT AGROINFILTRATION

CROSS-REFERENCE TO RELATED APPLICATIONS

This application claims the benefit of U.S. Provisional Application No. 61/090,221, filed Aug. 19, 2008, which is hereby incorporated by reference, in its entirety.

STATEMENT REGARDING FEDERALLY SPONSORED RESEARCH OR DEVELOPMENT

This invention was made with government support under Grant No. 0653984 awarded by the National Science Foundation. The government has certain rights in the invention.

BACKGROUND OF THE INVENTION

Biofuels such as ethanol are fermented from glucose, and the cellulose in biomass is a potential source of this sugar. However, a synergistic set of enzymes is needed to degrade the cellulose into glucose. Typically, these enzymes are produced by fungal cell culture which requires a high capital cost and a large number of bioreactors. Thus, there is a need for a more efficient system of enzyme production that requires lower capital costs, expends less energy, and emits less carbon dioxide.

BRIEF SUMMARY OF THE INVENTION

The present disclosure provides methods of producing a protein, such as a cellulase, by agroinfiltration. The method generally comprises first producing an *Agrobacterium* that contains a modified Ti plasmid encoding the cellulase. The *Agrobacterium* is combined with a plurality of plant cells to form a mixture and to allow infection of at least one plant cell of the plurality. A cellulase-containing fraction is recovered from the mixture after a period of time sufficient for the plant cells to express the cellulase. In one embodiment, the plurality of plant cells is within an intact plant. In another embodiment, the plurality of plant cells is within a detached plant part. In another embodiment, the period of time is at least 4 days. In one embodiment, at least 1 mg cellulase per kg fresh plant cell weight is expressed after the period of time is at least 4 days. In another embodiment, at least 2.6 mg cellulase per kg fresh plant cell weight is expressed after the period of time is at least 6 days. In one embodiment, the cellulase is from a thermophilic organism. In another embodiment, the cellulase is an exoglucanase. In another embodiment, the cellulase is an endoglucanase. In one embodiment, the endoglucanase is β-1,4-endoglucanase E1 from *Acidothermus cellulolyticus*. In one embodiment, the cellulase has an activity of at least 40,000 nmol MU/min/kg fresh plant tissue weight at a pH of 5.5 and a temperature of 65° C. In one embodiment, the *Agrobacterium* is *A. tumefaciens*. In one embodiment, recovering the cellulase-containing fraction comprises rupturing the plurality of plant cells. In another embodiment, expression of the cellulase is under the control of a constitutive promoter. In one embodiment, the constitutive promoter is 35S from cauliflower mosaic virus. In one embodiment, combining the *Agrobacterium* with a plurality of plant cells comprises pressure infiltration. In another embodiment, combining the *Agrobacterium* with a plurality of plant cells comprises vacuum infiltration. In one embodiment, the cellulase is thermostable. In one embodiment, the plurality of plant cells are from *Nicotiana benthamiana*. In one embodiment, the cellulase is linked to a signal peptide.

BRIEF DESCRIPTION OF THE DRAWINGS

FIG. 2 depicts the expected amino acid sequence from the β-1,4-endoglucanase translation product.

FIG. 12 depicts the lab-scale vacuum chamber used to infiltrate intact plants (left) or detached leaves (right).

DETAILED DESCRIPTION OF THE INVENTION

The following description sets forth numerous exemplary configurations, parameters, and the like. It should be recognized, however, that such description is not intended as a limitation on the scope of the present invention, but is instead provided as a description of exemplary embodiments.

1. Selection of Initial Target Enzyme and Secretion Signal Peptides

*Acidothermus cellulolyticus* is a thermophilic bacterium that lives in acidic environments. The β-1,4-endoglucanase E1 enzyme was selected from this organism because its ability to hydrolyze cellulose is inhibited at ambient temperatures, so in planta expression of this gene does not alter the plant's phenotype. Also, the endoglucanase has an optimal activity at pH 5.5, which is approximately the pH of the plant cell apoplast. Furthermore, several other research groups have successfully expressed this enzyme in stable transgenic plants. The sequence for E1 was obtained from the NIH Entrez cross-database search (accession number P54583). The mature protein (without the native secretion signal peptide) consists of 521 amino acids with an estimated molecular weight of 56,477 Da. The protein consists of a catalytic domain (E1-cd, ~40.3 kDa) and a cellulose-binding domain (E1-cbd, ~10.8 kDa), connected by a linker region (E1-link, ~5.4 kDa). The 41-amino-acid native signal peptide was replaced by the 25-amino-acid signal peptide from *Oryza sativa* α-amylase (Ramy3D SP) to facilitate secretion of the protein from plant cells to the apoplast.

2. Codon Optimization, Gene Synthesis

Figure 1:
FIG. 1 depicts a schematic of the gene synthesized by DNA 2.0, Inc. RAMY 3D SP encodes a signal peptide from rice alpha amylase. E1 is β-1,4-endoglucanase E1 from *Acidothermus cellulolyticus*. E1-cd encodes the E1 catalytic domain. E1-link encodes the E1 linker domain. E1-cbd encodes the E1 cellulose binding domain. PFT-6His encodes a peptide fusion tag, a 6 polyhistidine tag. Stop codons and restriction enzyme sites (XhoI, PstI, HindIII, and SpeI) have been added to flanking regions.

The gene for *A. cellulolyticus* β-1,4-endoglucanase E1 was codon-optimized for expression in *N. benthamiana* using the codon usage table for this plant from the KEGG database. A polyhistidine tag was added to the C-terminus of the protein to allow rapid purification by metal affinity chromatography. Appropriate restriction enzyme sites were added to allow insertion into our other expression cassettes. The entire 1,566 bp DNA fragment was chemically synthesized by an outside company (DNA 2.0, Inc., Menlo Park, Calif.) (FIG. 1).

3. Cloning into Binary Expression Vectors

The chemically synthesized E1 gene that encodes β-1,4-endoglucanase from *Acidothermus cellulolyticus* was provided by DNA 2.0 in the vector pJ210: 11772. The coding region of 552aa protein shown in FIG. 2 contains the 25aa Ramy3D signal peptide fused to the N-terminal and a 6aa his-tag at the C-terminal.

4. Cloning into the 35S Expression Vector (for Constitutive Expression)

Figure 3:
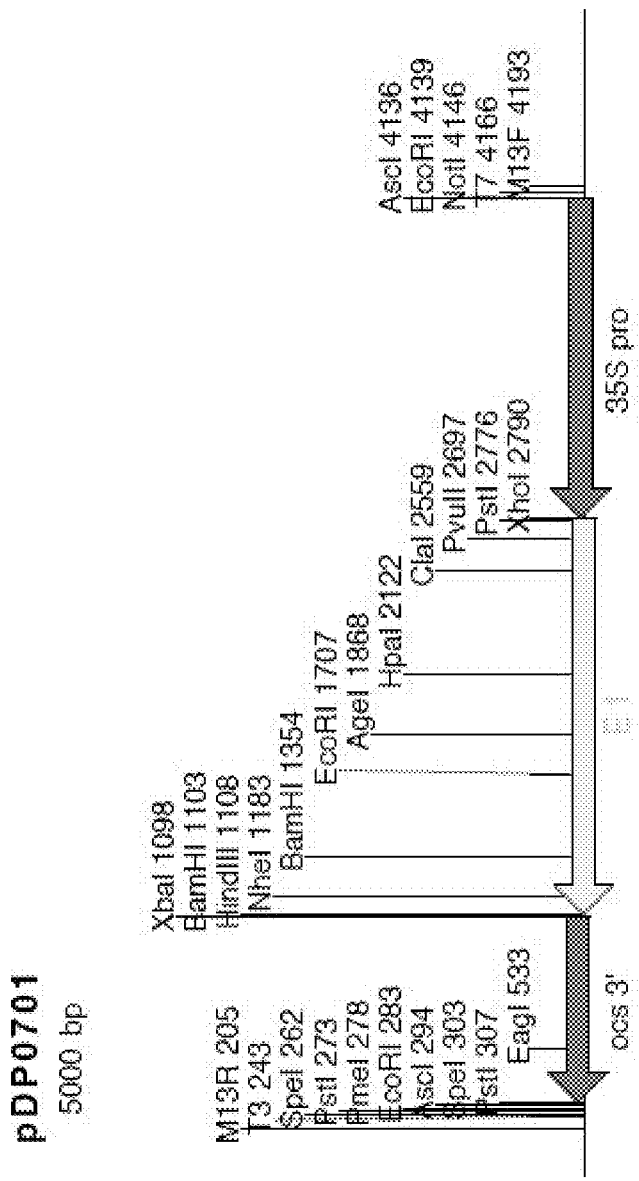
FIG. 3 depicts a map of the pDP0701 vector.
Figure 4:
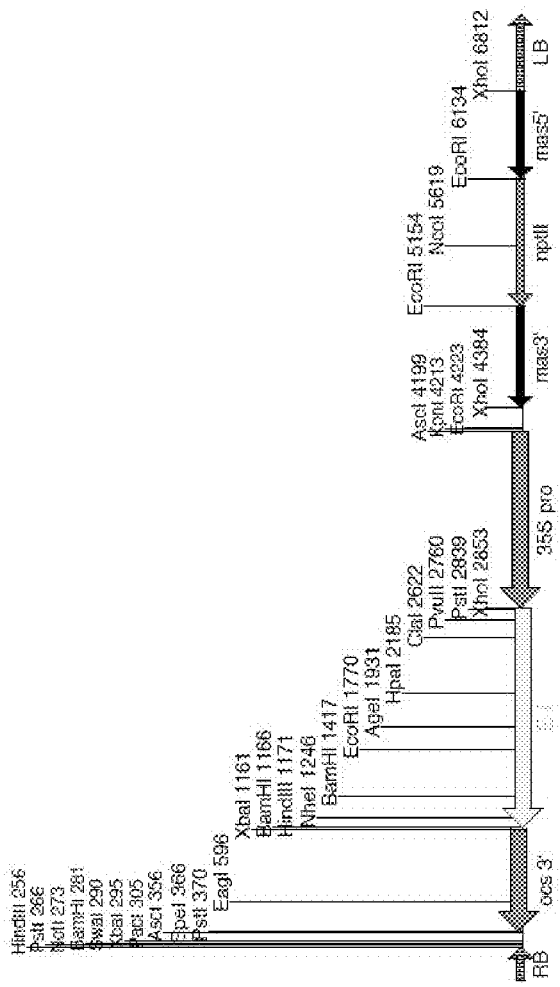
FIG. 4 depicts a map of the pDP07.0202a binary vector.

The vector pJ210: 11772 containing E1 was digested with the restriction endonucleases XhoI and HindIII at positions 1198 and 2872 respectively yielding a 1674 bp fragment that was directionally cloned into the shuttle vector pDE00.0113 creating the plasmid pDP0701. The E1 coding region was cloned downstream from a 35S promoter and upstream from an ocs3' regulatory sequence creating an E1 35S expression cassette. The E1 expression cassette in pDP0701 (FIG. 3) was excised by digestion with the endonuclease AscI and inserted into the binary vector pDU97.1005 creating the vector designated pDP07.0202a (FIG. 4).

5. Creation of Recombinant *Agrobacterium* Strains Containing the 35S Expression Cassette The binary plasmid pDP07.0202a was electroporated into the following two *Agrobacterium* strains, EHA105pCH32 and C58C1, resulting in two recombinant *Agrobacterium* (*Agrobacterium tumefaciens*) strains that can be used to transiently express the E1 protein in plant systems.

6. Production of Recombinant Cellulase Enzyme Using Transient Agroinfiltration in *N. benthamiana*

Figure 5:
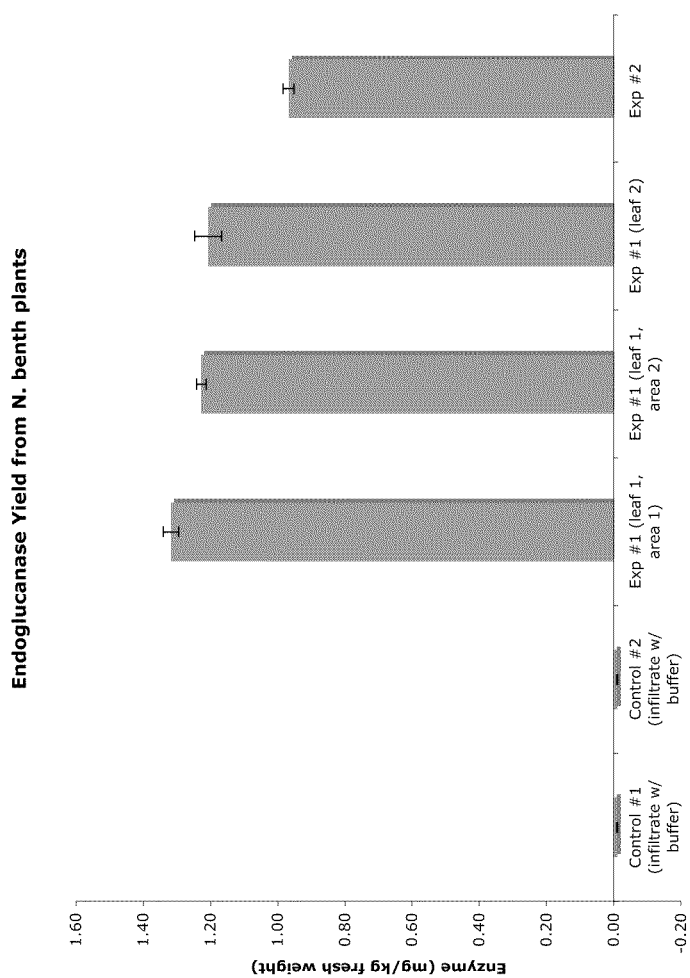
FIG. 5 depicts the amount of endoglucanase produced in various tissue samples from tobacco plants (*Nicotiana benthamiana*). Controls #1 and #2 are two different tobacco plants infiltrated with buffer but no bacteria. Experimental #1 and #2 are two different tobacco plants infiltrated with *Agrobacteria* suspended in buffer. Variability was examined between different areas of the same leaf and between leaves of experimental plant #1. Plant to plant variability was examined between experimental plants #1 and #2.

In the transient expression studies the recombinant EHA105pCH32 Agrobacterial strain with the constitutive CaMV 35S promoter was used. In this expression system, the E1 transcript is produced under the control of the strong 35S constitutive promoter. This strain of bacteria was cultured in the lab and used to infect four-week-old tobacco (*N. benthamiana*) plants. Infection could take place in the presence or absence of a gene silencing suppressor. The leaves of a 4 week old *Nicotiana benthamiana* plant were vacuum infiltrated. After four days, plant tissue was harvested, homogenized, extracted and tested for enzyme activity. Results are summarized in FIG. 5. The minimum amount of enzyme expressed after 4 days was approximately 1 mg cellulase per kg fresh plant cell weight. The activity corresponding to the amounts of enzyme shown in FIG. 5 ranged from 40,000 to 52,000 nmol MU/min/kg fresh plant tissue weight at pH 5.5 and at 65° C.

This experiment demonstrated a proof of principle that *A. tumefaciens* can be used to transiently (and rapidly) produce functional endoglucanase in plant tissue. Variability was observed between different tissues and different plants, but in general the yield was 1 mg of enzyme/kg fresh plant weight. Similar results were seen with this constitutive promoter for production of a different protein (human AAT) using this method (Sudarshana et al. *Plant Biotech J.* 4: 551-559 (2006)). However, when a viral amplified expression system was used to express AAT, a 70-fold yield increase was achieved, so it is expected that substantial improvements in productivity may be seen when a viral amplicon expression system is used. Also, the activity assay was used to show that the *A. tumefaciens* itself does not produce the enzyme, the plant tissue does. It was also demonstrated that his-tagged rE1 at the C terminal does not eliminate activity. Accordingly, one embodiment of this invention is the functional production of rE1 via transient agroinfiltration in plant tissues.

Figure 6:
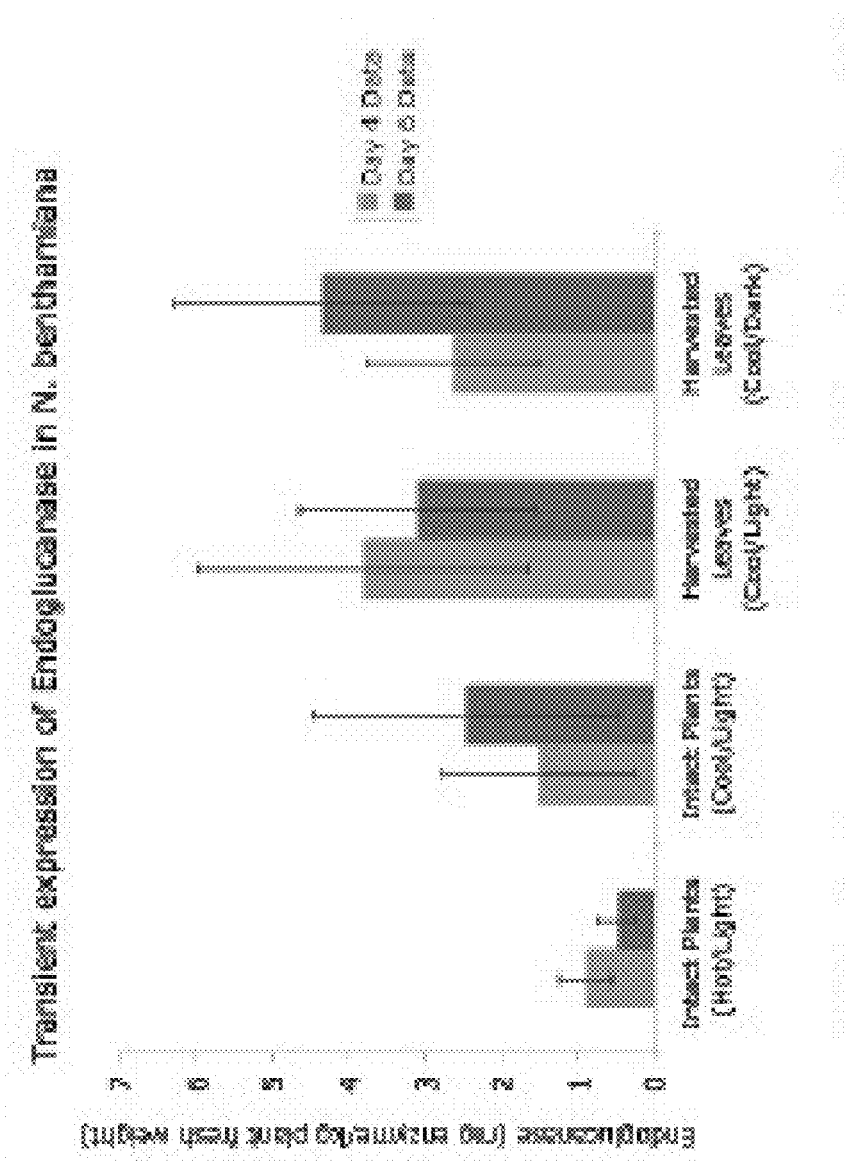
FIG. 6 depicts transient expression of endoglucanase in tobacco plants. The amount of endoglucanase was monitored over time in infiltrated intact plants and harvested leaves stored in different environments. Hot refers to maximum temperatures >30° C. Cool refers to maximum temperatures <30° C. Light refers to a 16 h/8 h light/dark cycle. Dark refers to 24 h darkness.
Figure 7:
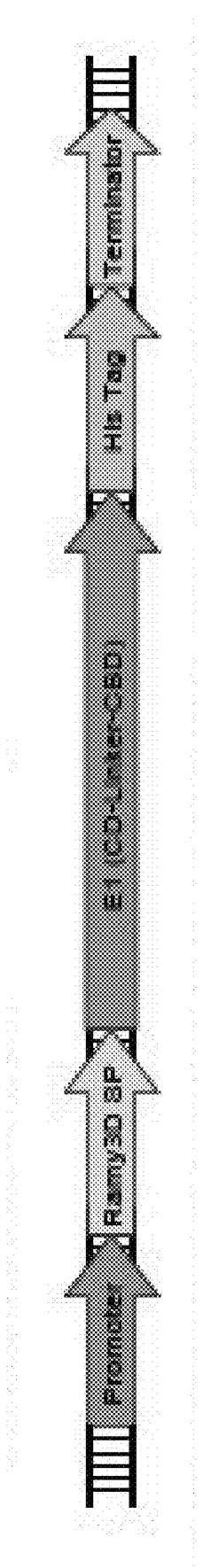
FIG. 7 depicts the modified gene for endoglucanase from *A. cellulolyticus*. The 35S promoter from Cauliflower Mosaic Virus facilitates constitutive transcription.
Figure 8:
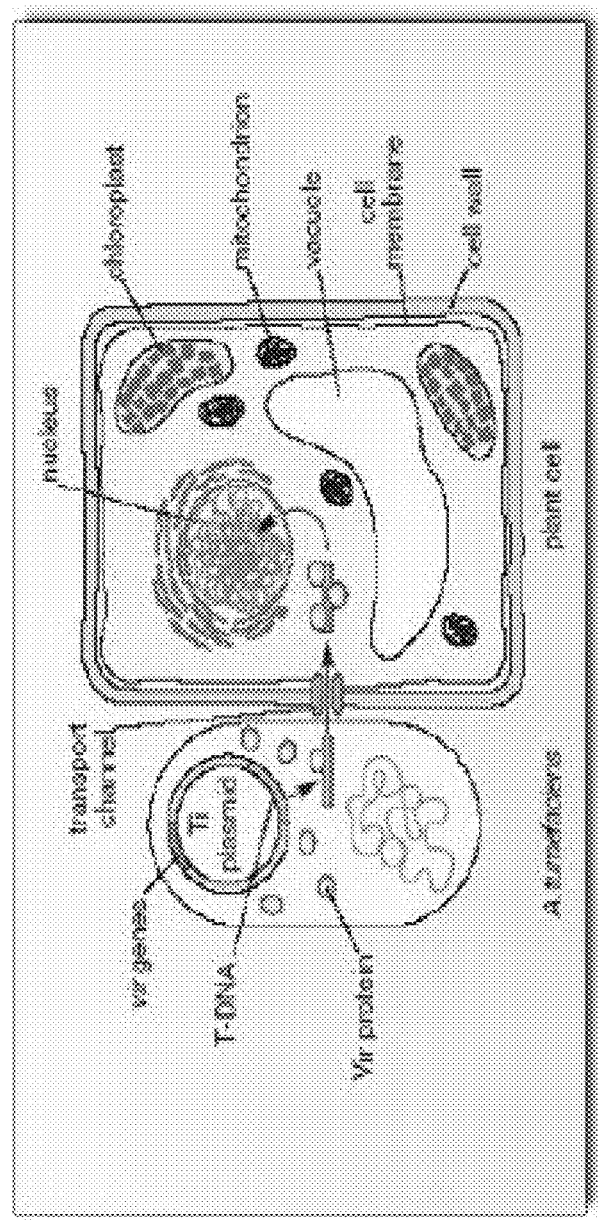
FIG. 8 depicts an *Agrobacterium* transferring a specific segment of its Ti plasmid into a plant cell.
Figure 9:
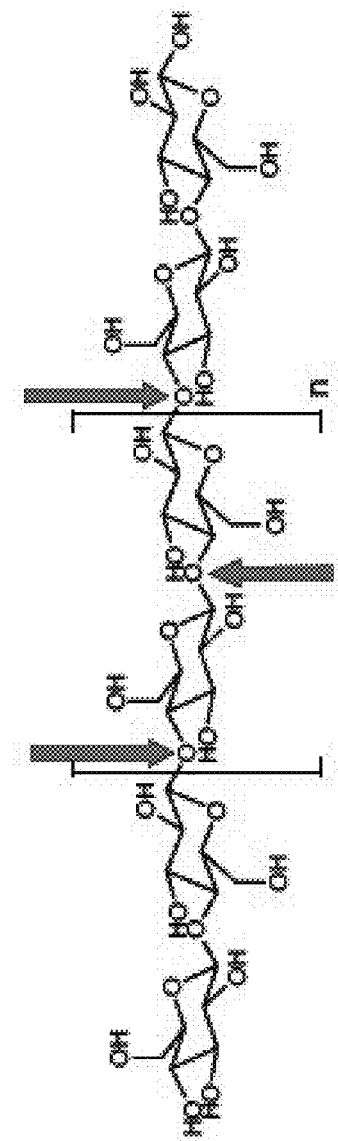
FIG. 9 depicts endoglucanase hydrolyzing β-1,4-glucosidic bonds within cellulose chains (arrows).
Figure 10:
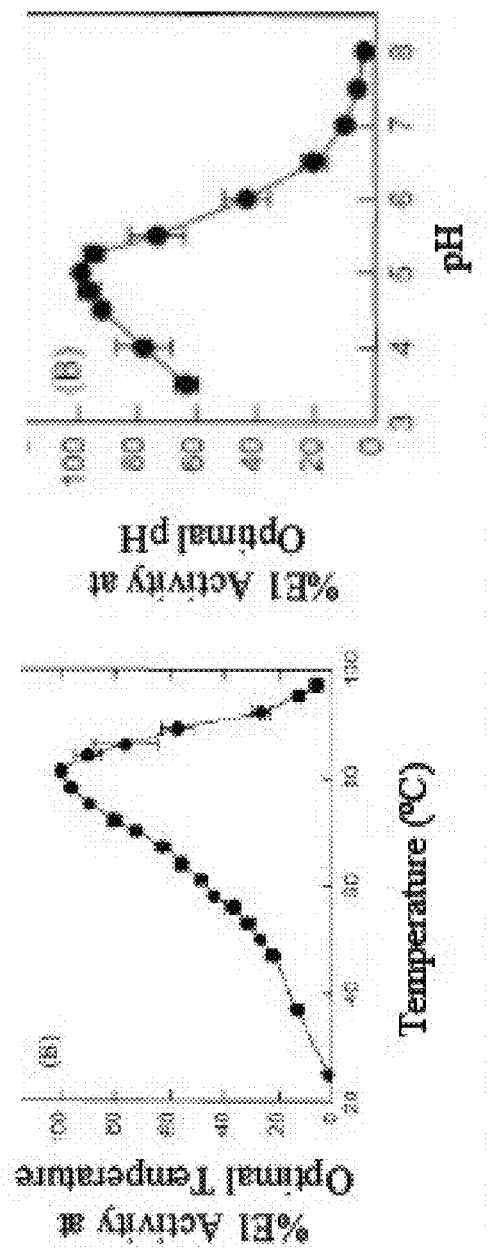
FIG. 10 depicts the optimal conditions for endoglucanase activity.
Figure 11:
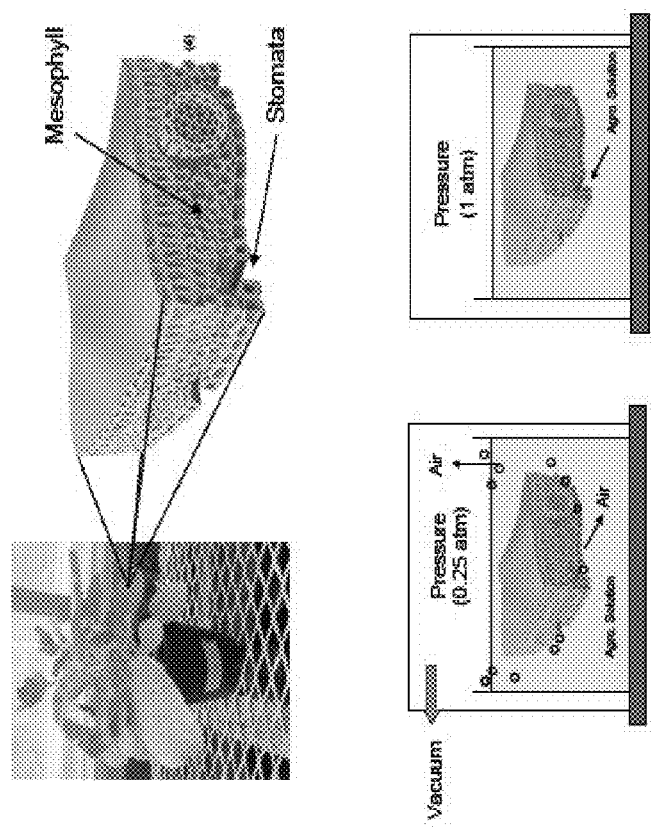
FIG. 11 depicts how vacuum infiltration brings *Agrobacteria* and plant cells together. The leaf tissue is immersed in a suspension of *Agrobacteria*, and a vacuum is pulled within the chamber. Air bubbles emerge from the leaf tissue and rise to the surface. The vacuum is released, and the liquid containing the *Agrobacteria* floods the tissue, bringing the bacteria in direct contact with the plant cells.
Figure 13:
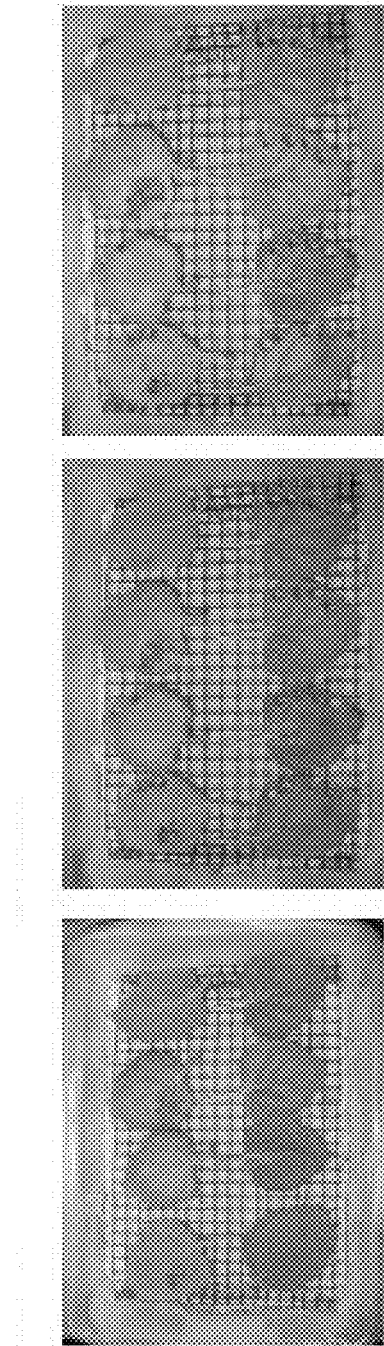
FIG. 13 depicts detached leaves 4 days (left), 6 days (middle), and 9 days (right) after infiltration with *Agrobacteria*.

It was also demonstrated that functional recombinant E1 can be produced in harvested *N. benthamiana* leaves, at even slightly higher expression levels (FIG. 6). In these transient expression studies, the EHA105pCH32 agrobacterial strain was used with the constitutive CaMV 35S promoter. This strain of bacteria was cultured in the lab and used to infect four-week-old tobacco (*N. benthamiana*) plants. The leaves of a 4 week old *Nicotiana benthamiana* plant were vacuum infiltrated. After four days, plant tissue was harvested, homogenized, extracted and tested for enzyme activity. The infiltrated plants and leaves were stored at various conditions to determine their effect on enzyme yield. Intact plants were stored in a hot greenhouse (daily high temperatures >30° C., 14 hours of light per day). To keep the harvested leaves alive, they were stored in a humid container at a constant temperature of 22° C. and protected from light. To make a valid comparison between the plants and leaves, some of each were stored adjacent to each other indoors, at ~25° C. with 16 hours of light per day. The leaves were stored in a humid container with a clear covering to allow illumination. Intact plants and harvested leaves were tested for enzyme activity after four and six days of incubation. The average amount of enzyme expressed after 6 days was approximately 2.6 mg cellulase per kg fresh plant cell weight. Activity assay results were converted to expression level (mg E1/kg fresh weight plant tissue) based on the reported specific activity of native E1.

In a further embodiment, activation of the cellulase in planta allows for in situ degradation of cellulose within the leaf tissue.

Although this E1 embodiment involves the specific example of transient agroinfiltration of rE1 in *N. benthamiana* using a constitutive expression system (CaMV 35S promoter), the approach can be used for production of any cellulose degrading enzyme, including, without limitation, other endoglucanases, exoglucanases, beta-glucosidases, and xylanases, multiple enzymes in the same host plant using co-infiltration, different host plants, and different promoters, plasmids, and expression systems.

We claim:

1. A method of producing a full-length cellulase by transient agroinfiltration, the method comprising:
   providing an *Agrobacterium*, the *Agrobacterium* comprising a Ti plasmid encoding the cellulase;
   combining the *Agrobacterium* with detached plant tissue using transient agroinfiltration to form a mixture and to allow infection of at least one plant cell of detached plant tissue;
   recovering a cellulase-containing fraction from the mixture after a period of time sufficient for the detached plant tissue to transiently express the cellulose; and
   recovering a functional full-length cellulase from the cellulase-containing fraction.

2. The method of claim 1, wherein the period of time is at least 4 days.

3. The method of claim 1, wherein the cellulase is from a thermophilic organism.

4. The method of claim 1, wherein the cellulase is an exoglucanase.

5. The method of claim 1, wherein the cellulase is an endoglucanase.

6. The method of claim 5, wherein the endoglucanase is β-1,4-endoglucanase E1 from *Acidothermus cellulolyticus*.

7. The method of claim 1, wherein the cellulase has an activity of at least 40,000 nmol MU/min/kg fresh plant tissue weight at a pH of 5.5 and a temperature of 65° C.

8. The method of claim 1, wherein the *Agrobacterium* is *A. tumefaciens*.

9. The method of claim 1, wherein recovering the cellulase-containing fraction comprises rupturing the cells of the plant tissue.

10. The method of claim 1, wherein expression of the cellulase is under the control of a constitutive promoter.

11. The method of claim 10, wherein the constitutive promoter is 35S from cauliflower mosaic virus.

12. The method of claim 1, wherein combining the *Agrobacterium* with detached plant tissue comprises pressure infiltration.

13. The method of claim 1, wherein combining the *Agrobacterium* with detached plant tissue comprises vacuum infiltration.

14. The method of claim 1, wherein the cellulase is thermostable.

15. The method of claim 1, wherein the plant tissue is from *Nicotiana benthamiana*.

16. The method of claim 1, wherein the cellulase is linked to a signal peptide.

17. The method of claim 1, wherein recovering a cellulase-containing fraction occurs within nine days of combining the *Agrobacterium* with the detached plant tissue.

18. The method of claim 6, wherein at least 1 mg cellulase per kg fresh plant cell weight is expressed within 4 days after infection of the at least one plant cell.

19. The method of claim 6, wherein at least 2.6 mg cellulase per kg fresh plant cell weight is expressed within 6 days after infection of the at least one plant cell.

20. The method of claim 6, wherein recovering a cellulase-containing fraction occurs within nine days of combining the *Agrobacterium* with the detached plant tissue.

21. The method of claim 20, wherein for each kilogram of the plant tissue combined with the *Agrobacterium* at least 2.6 mg of cellulase are recovered in the cellulase-containing fraction.

\* \* \* \* \*